United States Patent [19]

Carrico et al.

[11] 4,259,233

[45] Mar. 31, 1981

[54] β-GALACTOSYL-UMBELLIFERONE-LABELED PROTEIN AND POLYPEPTIDE CONJUGATES

[75] Inventors: Robert J. Carrico; That T. Ngo, both of Elkhart, Ind.

[73] Assignee: Miles Laboratories, Inc., Elkhart, Ind.

[21] Appl. No.: 87,522

[22] Filed: Oct. 23, 1979

[51] Int. Cl.$^3$ .......................... C07G 7/00; C07G 3/00; C07C 103/52
[52] U.S. Cl. ...................................... 260/112 B; 536/4; 260/112.5 R; 260/112 R; 260/121; 424/85; 435/188
[58] Field of Search ..................... 260/112.5 R, 112 B; 536/4

[56] References Cited

U.S. PATENT DOCUMENTS 4,182,856  1/1980  Buckler ........................ 260/112.5 R Primary Examiner—Delbert R. Phillips
Attorney, Agent, or Firm—Andrew L. Klawitter

[57] ABSTRACT

A β-galactosyl-umbelliferone-labeled conjugate of the formula:

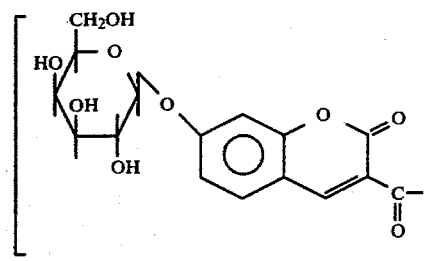

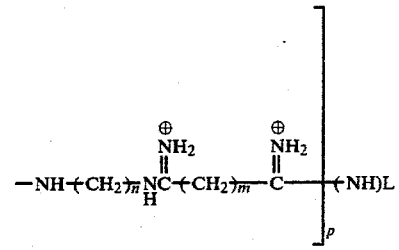

wherein $-(NH)L$ is a protein or polypeptide, such as an immunoglobulin, bound through an amino group thereof, n is an integer from 2 through 10, m is an integer from 1 through 10, and p is on the average from 1 to the number of available amino groups in L. An intermediate in the synthesis of such labeled conjugate is also provided. The labeled conjugates are useful as reagents in specific binding assays (e.g., immunoassays) for determining the conjugated protein or polypeptide, or a specific binding analog or partner thereof, in liquid media.

11 Claims, 1 Drawing Figure

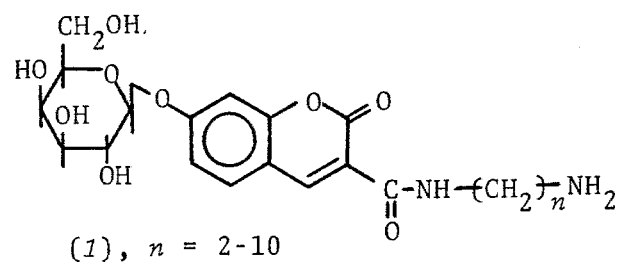
(1), n = 2-10
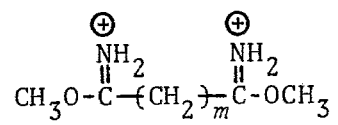
m = 1-10
immunoglobulin (Ig)
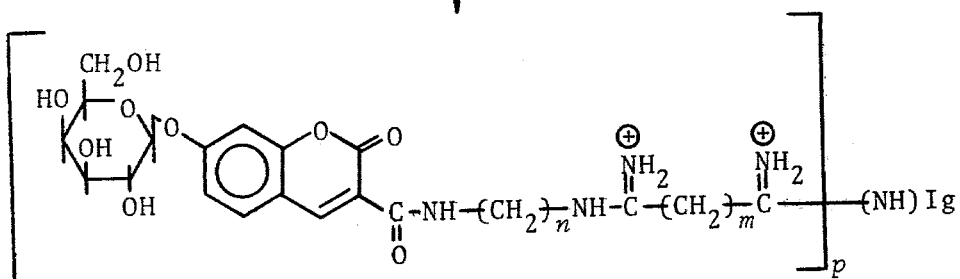
(2a,b,c), n = 2-10, m = 1-10, p = 1-20
(2a), Ig = IgG
(2b), Ig = IgA
(2c), Ig = IgM
TABLE I

β-GALACTOSYL-UMBELLIFERONE-LABELED PROTEIN AND POLYPEPTIDE CONJUGATES

BACKGROUND OF THE INVENTION

1. Field of the Invention

This invention relates to nonradioisotopically-labeled proteins and polypeptides useful as labeled conjugates in specific binding assays for determining such proteins and polypeptides, or specific binding partners thereof, in liquid media such as body fluids, particularly serum. In particular, the present invention relates to β-galactosyl-umbelliferone-labeled proteins (e.g., immunoglobulins) and polypeptides useful in nonradioisotopic immunoassays.

2. Description of the Prior Art

Nonradioisotopic specific binding assays employing an enzyme-cleavable substrate label are described in German Offenlegungschriften Nos. 2,618,419 and 2,618,511, corresponding respectively to U.S. patent applications Ser. Nos. 667,982 and 667,996, both filed Mar. 18, 1976, and assigned to the present assignee. The assays avoid the use of radioisotopic labels and can be performed in homogeneous or heterogeneous formats. In the heterogeneous format, the bound- and free-species of the labeled conjugate are physically separated and the label measured in one of the separated species, whereas in the homogeneous format, the label expresses a different activity in the bound-species compared to the free-species, permitting performance of the assay without a separation step. In the aforementioned assays, the labeled conjugate serves as a substrate for a cleaving enzyme, with cleavage of the conjugate producing a distinguishable indicator product, usually a fluorescent product. The fluorescers umbelliferone or fluorescein are coupled to the ligand under assay through an ester bond which upon cleavage by an esterase releases the free fluorescent products, umbelliferone and fluorescein, respectively.

An improved substrate-labeled specific binding assay is described in pending U.S. patent application Ser. No. 886,094, filed Mar. 13, 1978, and assigned to the present assignee. The improvement comprises employing as the label component of the labeled conjugate, a residue of the formula:

G—D—R wherein G is a glycone, D is a dye indicator moiety, and R is a linking group through which the dye indicator moiety is covalently bound to the binding component (usually the ligand under assay or a binding analog thereof) of the labeled conjugate. The cleavage enzyme employed is a glycosidase which cleaves the bond between the glycone and the dye indicator moiety, releasing a detectable, usually fluorescent, fragment comprising the dye indicator moiety coupled to said binding component (e.g., the ligand). Most preferably, the glycone is a β-galactosyl group and the dye indicator moiety is umbelliferone.

Various β-galactosyl-umbelliferone-labeled ligand conjugates are specifically described in the aforesaid Ser. No. 886,094 wherein the labeled ligand is a nonproteinaceous hapten of molecular weight less than 1000. It is highly desirable to prepare β-galactosyl-umbelliferone-labeled conjugates for proteins and polypeptides of clinical significance so as to enable the homogeneous, nonradioisotopic specific binding assay determination of such proteins and polypeptides, and their binding partners. Preparation of such labeled protein and polypeptide conjugates is complicated by the complex structure and heterogeneity of proteins and polypeptides; the molecular size, fragility, and suceptibility to denaturation of such ligands; the need to maintain water solubility in the labeled conjugates; the need to maintain proper configuration in the conjugated protein or polypeptide; and the expected instability of chemically modified proteins and polypeptides over long storage periods.

The numerous conventional methods for modifying proteins and polypeptides and for coupling such ligands to solid supports and other materials are described in the following: for general reviews see *Methods of Enzymology*, vol. XLIV "Immobilized Enzymes," ed. Mosbach, Academic Press (New York 1976), *Affinity Chromatography*, Lowe and Dean, John Wiley and Sons (New York 1974), and *Clin. Chem.* 22:726 (1976); and for specific references see *Science* 144:1344 (1967) [the carbodiimide reaction], Erlanger et al, *Methods in Immunology and Immunochemistry*, ed. Williams and Chase, Academic Press (New York 1967), p. 149 [the mixed anhydride reaction], *Peptides and Amino Acids*, Kopple, W. A. Benjamin, Inc. (New York 1966) [the acid azide and active ester reactions], and *Proc. Nat. Acad. Sci. USA* 66:651 (1970) [the bis-imidate reaction].

SUMMARY OF THE INVENTION

The present invention provides β-galactosyl-umbelliferone-labeled proteins and polypeptides of the general formula:

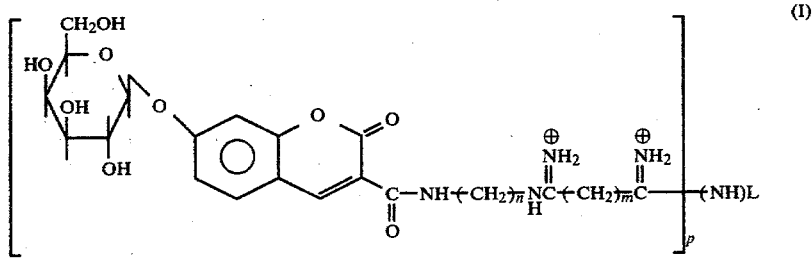

wherein —(NH)L is a protein or polypeptide bound through an amino group thereof, n is an integer from 2 through 10, m is an integer from 1 through 10, and p is on the average from 1 through the number of available amino groups in L.

The present labeled conjugates are prepared by coupling the desired protein or polypeptide to N-(ω-aminoalkyl)-7-β-galactosylcoumarin-3-carboxamides in the presence of bifunctional bis-imidates, as described in detail below. The labeled conjugates are used as reagents in the known homogeneous and heterogeneous specific binding assays, particularly immunoassays, employing β-galactosyl-umbelliferone-labeled protein and polypeptide conjugates, are relatively well-characterizable due to the relative selectivity of the bis-imidate coupling technique despite the heterogeneity of the functional groups on the ligands involved, and are sufficiently water soluble and stable to enable their use as assay reagents in commercial test kits.

DESCRIPTION OF THE PREFERRED EMBODIMENTS

The labeled conjugates (I) of the present invention are prepared by coupling the desired protein or polypeptide to N-(ω-aminoalkyl)-7-β-galactosylcoumarin-3-carboxamides of the formula:

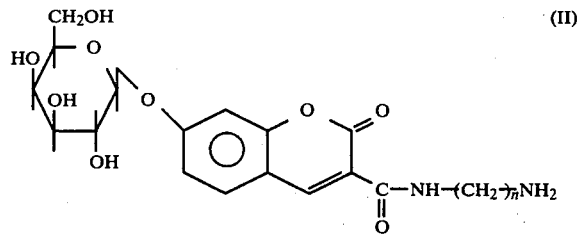

(II)

wherein n is as defined above, in the presence of a bifunctional bis-imidate of the general formula:

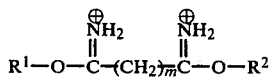

(III)

wherein m is as defined above and $R^1$ and $R^2$, which may be the same or different but which more usually are the same, are alkyl, preferably lower alkyl (i.e., having 1-4 carbon atoms) such as methyl, ethyl, n-propyl, isopropyl, and so forth. Particularly preferred bis-imidates (III) are the dimethyl alkylimidates, especially dimethyl adipimidate. The bis-imidates are generally available from commercial sources or may be prepared by published methods by those having ordinary skill in the art [Hunter and Ludwig, *J. Am. Chem. Soc.* 84:3491 (1962)]. The bis-imidates will normally be provided in a suitable salt form which upon dissolution in the aqueous reaction media generates the positively charged bis-imidate species (III). Correspondingly, isolation of the labeled conjugate (I) from aqueous media such as by solvent evaporation or precipitation yields salts forms of the bis-imidates (III) wherein the counter anions to the protonated imino groups are taken from available anions in the media.

The coupling reaction is allowed to proceed in aqueous solution under mild conditions, e.g., at a pH between about 7 and about 10, more usually between 8 and 9, and at temperatures between about 0° C. and about 40° C., more usually between 20° C. and 30° C. Usually, the amino-functionalized carboxamide (II), the bis-imidate (III), and the desired protein or polypeptide to be labeled are added in sequence, with a short incubation period for reaction between the carboxamide and the bis-imidate of between 1 and 30 minutes, followed by addition of the protein or polypeptide and a second incubation period lasting between 10 minutes and 4 hours.

It has been generally found that the longer the second incubation period, the greater the degree of substitution of the β-galactosyl-umbelliferone labeling moiety on the protein or polypeptide, i.e., the higher the value of p in formula (I). The upper limit on the number of β-galactosyl-umbelliferone moieties that can be introduced to a given protein or polypeptide is theoretically limited only by the number of available amino groups in such protein or polypeptide. By available amino groups is meant those amino groups which are reactive with the bis-imidate coupling agent. Under the current state of knowledge, such amino groups comprise (a) the terminal α-amino groups of the peptide chain in the protein or polypeptide and (b) the ε-amino groups of lysyl residues occurring in the protein or polypeptide. The degree of substitution (i.e., the value of p) of the labeling moiety will vary between 1 and such theoretical upper limit depending on the characteristics desired for the labeled conjugate in the assay method contemplated. Normally, p will be on the average between 1 and 100, more usually between 1 and 20.

The aforementioned amino-functionalized carboxamides (II) can be prepared by condensation of 7-β-galactosylcoumarin-3-carboxylic acid [Burd et al, *Clin. Chem.* 23:1402(1977)] with an appropriate α,ω-alkanediamine wherein the alkane is selected from the linear series having between 2 and 8 carbon atoms, e.g., ethylene diamine, 1,6-hexanediamine, 1,8-octanediamine, and so forth. The condensation reaction preferably is carried out in the presence of a carboxyl-activating reagent such as a carbodiimide, as is known in the art. This method of preparing the carboxamides (II) produces significant amounts of side products, particularly the bis-β-galactosyl-umbelliferone product resulting upon reaction of a second 7-β-galactosylcoumarin-3-carboxylic acid molecule with a previously formed carboxamide (II). Such side products can be removed by conventional methods, particularly chromatography, to permit isolation of the carboxamide (II) for coupling to the desired protein or polypeptide.

The formation of significant side products in the preparation of the carboxamides (II) can be substantially eliminated by following an alternative route wherein an N-substituted α,ω-alkanediamine is used in the condensation with 7-β-galactosylcoumarin-3-carboxylic acid. In this way, only a single amino group is available on the alkanediamine for reaction with the acid, preventing formation of the bis-β-galactosyl-umbelliferone product. Appropriately substituted alkanediamines are the N-(alkyloxycarbonyl)-α,ω-alkanediamines, e.g., the N-(tert-butyloxycarbonyl)-α,ω-alkanediamines. The functionalized carboxamide is then treated to remove the N-blocking group, yielding the amino-functionalized carboxamide (II).

It is evident that numerous functional equivalents of the labeled conjugates (I) can be prepared by one with ordinary skill in the art without departing from the inventive features hereof. For example, the umbelliferyl residue can be substituted, particularly at its 4, 5, 6 or 8 positions with appropriate groups while not substantially altering the ability of the modified labeled conjugate to act as a substrate for β-galactosidase or to be bound by a binding partner, e.g., antibody, to the labeled protein or polypeptide. Likewise, derivatization of the linking group between the umbelliferyl moiety and the conjugated protein or polypeptide will also produce equivalent compounds. Such equivalents will have the same function as labeled conjugates (I) and can be prepared by appropriate selection of starting materials or appropriate chemical modification after formation of such labeled conjugates. Representative of the types of substituents that can be inserted to form equivalent compounds include, without limitation, lower alkyl, e.g., methyl, ethyl and butyl; halo, e.g., chloro and bromo; nitro; carboxyl; carbo lower alkoxy, e.g., carbomethoxy and carbethoxy; amino; mono- and di-lower alkylamine, e.g., methylamino, dimethylamino and methylethylamino; amido; hydroxyl; lower alkoxy, e.g., methoxy and ethoxy; and so forth.

The protein or polypeptide to be labeled according to the present invention will be antigenic, that is, capable of stimulating antibody production upon injection into a host animal or, in the case of the smaller polypeptides, will be capable of being rendered antigenic by coupling to an appropriate carrier, such as albumin, as is well-known in the art. The molecular weight of the protein or polypeptide will usually be between 130 and 10,000,000, more usually between 1,000 and 1,000,000.

Particular proteins and polypeptides may have widely varying biological functions, encompassing hormones, enzymes, transport proteins, receptor proteins, and immunoglobulins (e.g., antibodies). All proteins and polypeptides of clinical significance are contemplated for labeling according to the present invention since any particular protein or polypeptide will have available (e.g., a terminal $\alpha$-amino group or a lysyl $\epsilon$-amino group), or can be modified to make available, an amino group for coupling to the $\beta$-galactosyl-umbelliferone moiety by the bis-imidate technique. An amino-functionalized derivative of a protein or polypeptide of clinical significance will of course will be considered a protein or polypeptide in a true sense and in accordance with the use of such terms herein. Moreover, proteins and complex polypeptides (a polypeptide is conventionally defined as a polymer of amino acids joined by amide linkages, forming chains that can consist of as few as two or as many as several thousand amino acid residues) will contain several terminal $\alpha$-amino groups available for coupling. Furthermore, it is understood that substantially all proteins and most polypeptides contain one or more lysyl residues, making available $\epsilon$-amino groups thereof for coupling. Accordingly, proteins and polypeptides as a class can be labeled in the manner of the present invention and used as labeled conjugates in specific binding assays.

Particular polypeptides that can be labeled according to the present invention are angiotensin I and II, C-peptide, oxytocin, vasopressin, neurophysin, gastrin, secretin, glucagon, bradykinin and relaxin. Proteins contemplated by the present invention include the classes of protamines, mucoproteins, glycoproteins, globulins, albumins, scleroproteins, phosphoproteins, histones, lipoproteins, chromoproteins, and nucleoproteins. Examples of specific proteins are prealbumin, $\alpha_1$-lipoprotein, human serum albumin, $\alpha_1$-acid glycoprotein, $\alpha_1$-antitrypsin, $\alpha_1$-glycoprotein, transcortin, thyroxine binding globulin, haptoglobin, hemoglobin, myoglobin, ceruloplasmin, $\alpha_2$-lipoprotein, $\alpha_2$-macroglobulin, $\beta$-lipoprotein, erythropoietin, transferin, homopexin, fibrinogen, the immunoglobulins such as IgG, IgM, IgA, IgD, and IgE, and their fragments, e.g., $F_c$ and $F_{ab}$, complement factors, prolactin, blood clotting factors such as fibrinogen, thrombin and so forth, insulin, melanotropin, somatotropin, thyrotropin, follicle stimulating hormone, leutinizing hormone, gonadotropin, thyroid stimulating hormone, placental lactogen, intrinsic factor, transcobalamin, serum enzymes such as alkaline phosphatase, lactic dehydrogenase, amylase, lipase, phosphatases, cholinesterase, glutamic oxaloacetic transaminase, glutamic pyruvic transaminase, and uropepsin, endorphins, enkephalins, protamine, tissue antigens, bacterial antigens, and viral antigens such as hepatitis associated antigens (e.g., $HB_sAg$, $HB_cAg$ and $HB_eAg$).

Labeled protein and polypeptide conjugates prepared according to the present invention have been found to be of relatively well-characterizable structure due to the relative selectivity of the bis-imidate coupling reaction despite the heterogeneity of the functional groups on the proteins and polypeptides involved. Reproducibility in the synthesis of the complex conjugates permits their controlled manufacture on a large scale for incorporation in commercial test kits. The conjugates serve as useful reagents in homogeneous specific binding assays, it having been confirmed that even where the labeled material is a high molecular weight protein (e.g., an immunoglobulin), the enzyme substrate activity of the $\beta$-galactosyl-umbelliferone-labeled conjugates is significantly altered upon binding with antibody to the protein. Sufficient water solubility and stability is exhibited by the conjugates to permit their use in commercial test kits. Of particular note is the fact that the presence of positively charge imino groups in the labeled conjugates is understood to greatly assist maintenance of proper conformation of the labeled protein or polypeptide.

The present invention will now be illustrated, but is not intended to be limited, by the following examples.

EXAMPLE 1

Preparation of $\beta$-Galactosyl-umbelliferone-labeled IgG

The conjugates are prepared according to the reaction sequence shown in Table 1 in the drawing. This synthetic route is exemplified by the following method of preparing labeled conjugate (2a) wherein n=6, m=4, and p is on the average between 5 and 8.

N-(6-Aminohexyl)-7-$\beta$-galactosylcoumarin-3-carboxamide (1)

1,6-Hexanediamine (1.76 g, 15 mmoles) was dissolved in 20 milliliters (ml) of distilled water and the pH was adjusted to 9 with concentrated hydrochloric acid. 7-$\beta$-Galactosyl-coumarin-3-carboxylic acid (1.83 g, 5 mmoles) [Burd et al., Clin. Chem. 23:1402(1977)] was dissolved in the hexanediamine solution and the pH was further adjusted to 5±0.5. This solution was cooled to 4° C. in an ice bath. 1-Ethyl-3-(3-dimethylaminopropyl)carbodiimide (1.16 g, 6.15 mmoles) [Pierce Chemical Co., Rockford, Ill.] was added to the cooled solution and the pH was maintained at 5±0.5 manually. The reaction was allowed to proceed at 4° C. for two hours and then two more hours at room temperature. At the end of four hours, 80 ml water and 0.6 g (3.2 mmoles) 1-ethyl-3-(3-dimethylaminopropyl)carbodiimide were added to the reaction solution and the pH was maintained at 5. The solution was stirred continuously overnight at room temperature. Then it was diluted to 6 liters (L) with distilled water and applied onto a column (5×40 cm) of CM-Sepharose CL in the ammonium form [Pharmacia Fine Chemicals, Piscataway, N.J.]. The column was washed successively with 3 L distilled water, 1 L of 1 mM ammonium bicarbonate and 2 L of 2 mM ammonium bicarbonate. The chromatogram was developed with a linear gradient generated with 4 L of 2 mM and 4 L of 300 mM ammonium bicarbonate and 10 ml fractions were collected. The absorbance of the eluate was monitored at 280 nanometers (nm) and selected fractions were examined by thin layer chromatography on silica gel 60 plates using a 0.5 M triethylammonium bicarbonate, pH 7.8: ethanol (3:7) solvent. The fractions eluted between 70 and 90 mM ammonium bicarbonate showed several fluorescent spots when viewed under long wavelength UV light and one spot, $R_f=0.24$, gave a positive reaction with ninhydrin. These fractions were pooled and evaporated to dryness. The residue was dissolved in water and evaporated to dryness several times to remove the residual ammonium bicarbonate. The yield was less than 10%.

β-Galactosyl-umbelliferone-labeled IgG (2a)

To 8.5 mg (18 μmoles) of the above product in 2 ml of distilled water was added 10 mg (40 μmoles) dimethyl adipimidate dihydrochloride [Pierce Chemical Co., Rockford, Ill.] and 40 microliters (μl) triethylamine. The solution was stirred at room temperature for ten minutes and then 40 mg (0.26 μmole) human IgG [Miles Laboratories, Inc., Elkhart, Ind.] in 1 ml of 0.1 M sodium pyrophosphate buffer, pH 8.5, was added. The solution was stirred at room temperature for two additional hours, after which the solution was applied onto a column (3×50 cm) of Sephadex G-25 coarse, equilibrated with 0.1 M sodium phosphate pH 7.0. Fractions of 7 ml were collected. They were monitored at 280 and 340 nm and those containing IgG were pooled and dialyzed at 4° C. successively against 6 L of 0.1 M sodium phosphate, pH 7.0; 6 L of 0.1 M sodium phosphate, pH 7.0, containing 1 M sodium chloride; and 6 L of 0.1 M sodium phosphate, pH 7.0, for 18 hours each.

The above described synthesis of the β-galactosyl-umbelliferone-IgG conjugate (2a), n=6, m=4, can be modified to yield labeled conjugates wherein n=2–10 and m=1–10 by replacing the starting materials 1,6-hexanediamine and dimethyl adipimidate, respectively, with the appropriate α,ω-alkanediamine and dimethyl alkyldiimidate as follows:

| n | α,ω-alkanediamine |
|---|---|
| 2 | ethylenediamine |
| 3 | 1,3-propanediamine |
| 4 | 1,4-butanediamine |
| 5 | 1,5-pentanediamine |
| 7 | 1,7-heptanediamine |
| 8 | 1,8-octanediamine |
| 9 | 1,9-nonanediamine |
| 10 | 1,10-decanediamine |

| m | dimethyl alkyldiimidate |
|---|---|
| 1 | dimethyl malonimidate |
| 2 | dimethyl succinimidate |
| 3 | dimethyl glutarimidate |
| 5 | dimethyl pimelimidate |
| 6 | dimethyl octanediimidate |
| 7 | dimethyl nonanediimidate |
| 8 | dimethyl decanediimidate |
| 9 | dimethyl undecanediimidate |
| 10 | dimethyl dodecanediimidate |

EXAMPLE 2

Preparation of β-Galactosyl-umbelliferone-labeled IgA and IgM

The conjugates are prepared according to the reaction sequence shown in Table 1 in the drawing except that the amino-functionalized intermediate (1) was prepared by an alternate route. This synthetic route is exemplified by the following method of preparing labeled conjugates (2b) and (2c) wherein n=6, m=4, and p is on the average between 1 and 20.

N-(6-Aminohexyl)-7-β-galactosylcoumarin-3-carboxyamide (1)

A mixture of 3.68 g (0.01 mol) of 7-β-galactosylcoumarin-3-carboxylic acid, supra, 2.30 g (0.02 mol) of N-hydroxy-succinimide, and 2.27 g (0.011 mol) of dicyclohexylcarbodiimide in 25 ml of dimethylformamide (DMF) was stirred under argon at room temperature for 1 hour. A thick precipitate of dicyclohexylurea formed and was removed by filtration. The clear filtrate was combined with 2.52 grams (g) of the hydrochloride salt of N-(tert-butyloxycarbonyl)-1,6-hexanediamine [Stahl et al, *J. Org. Chem.* 43:2285(1976)]. The solution was cooled to 0° C. and 2.8 ml (2.02 g, 0.02 mol) of triethylamine was added. The reaction was allowed to stir at room temperature for 2 hours, then filtered to remove the precipitate of triethylamine hydrochloride. Evaporation of the DMF under reduced pressure gave an oily residue that was stirred for 15 minutes with 100 ml of 2 N hydrochloric acid. The heavy precipitate that formed was filtered, washed with water, and dried.

The precipitate was then taken up in methanol and combined with 25 g of silica gel 60 (E. Merck, Darmstadt, West Germany). The methanol was removed on a rotary evaporator and the impregnated silica gel placed atop a column of 200 g of silica gel made up in ethyl acetate. The column was eluted with a gradient of 2 L of ethyl acetate to 2 L of 1:1 volume:volume (v:v) ethyl acetate:ethanol, and 17 ml fractions were collected. Fractions 128 and 270 were combined, evaporated, and the residue recrystalized from isopropanol to give 3 g (53% yield) of N-[6-N-tert-butyloxycarbonylamino)-hexyl]-7-β-galactosylcoumarin-3-carboxamide as a white solid, mp 144°–146° C.

Analysis: Calculated for $C_{23}H_{38}N_2O_{11}$: C, 57.23; H, 6.76; N, 4.94. Found: C, 57.27; H, 6.64; N, 5.03. NMR Spectrum (d$_6$-DMSO): δ 1.4 (s, 9H).

The intermediate (2.83 g, 0.005 mol) was dissolved in 10 ml of cold (−10° C.) trifluoroacetic acid. After 2 hours, the trifluoroacetic acid was removed at 0° C. under high vacuum. The residue was taken up in 30 ml of water and applied to a 2.5 cm by 30 cm column of AG 1×8 ion exchange resin (chloride form, Bio-Rad Laboratories, Richmond, Calif.). One liter of water was passed through the column. The effluent was collected and evaporated to give a white solid. It was triturated with 400 ml of boiling methanol, filtered, and dried to give 2 g (40% yield) of the hydrochloride salt of N-(6-aminohexyl)-7-β-galactosylcoumarin-3-carboxamide (1), mp 234°–235° C.

Analysis: Calculated for $C_{22}H_{30}N_2O_9 \cdot HCl$: C, 52.54; H, 6.21; H, 5.57. Found: C, 52.52; H, 6.11; N, 5.47.

β-Galactosyl-umbelliferone-labeled IgA (2b)

Thirteen milligrams (26 μmole) of N-(6-aminohexyl)-7-β-galactosylcoumarin-3-carboxamide (1) was dissolved in 0.5 ml water and 7 mg (29 μmole) of dimethyl adipimidate dihydrochloride was added followed by 5 μl (35 μmole) of triethylamine. This mixture was allowed to stand at room temperature for 6.5 minutes and then was added to 2 ml of IgA (10 mg/ml) in 0.1 M sodium pyrophosphate, pH 8.5. After 3 hours, 0.5 ml of the reaction mixture was chromatographed on a 10 ml column of Sephadex G-25 [Pharmacia Fine Chemicals, Piscataway, N.J.] equilibrated with 0.1 M sodium phosphate buffer, pH 7.0, containing 0.02% sodium azide. Approximately 1 ml fractions were collected and fractions 4-6 were pooled. The pool was dialyzed against 1 L of 0.1 M sodium phosphate buffer, pH 7.0, containing 0.02% sodium azide for 20 hours. Then the dialysis was continued for 20 hours with the buffer containing 1.0 M sodium chloride and finally the dialysis was continued for 24 hours with buffer without sodium chloride. The labeled IgA (2b) had optical absorption maxima at 278 and 340 nm. During hydrolysis with $\beta$-galactosidase, the 340 nm absorbance decreased and a new band appeared at 405 nm.

$\beta$-Galactosyl-umbelliferone-labeled IgM (21 c)

To a solution (0.013 g in 0.4 ml water) of N-(6-aminohexyl)-7-$\beta$-galactosylcoumarin-3-carboxamide (1) were sequentially added 100 $\mu$l of triethylamine and 0.007 g of dimethyl adipimidate dihydrochloride. The mixture was stirred briefly and allowed to react for 5 minutes. Then, 4 ml of a 5.5 mg/ml solution of IgM in 0.1 M sodium pyrophosphate, pH 8.5, was added to the reaction mixture. After 5-10 minutes, the reaction was stopped by passing the mixture through a column of Sephadex G 25. The protein fractions were pooled and intensively dialyzed against 0.1 M sodium phosphate, pH 7.0.

EXAMPLE 3

Assay for IgG

A. Assay Reagents

1. Antiserum—Rabbit anti-human IgG obtained from Calbiochem, La Jolla, Calif.

2. Enzyme—*E. Coli* grade IV $\beta$-galactosidase was used (Worthington Biochemicals, Co., Freehold, N.J.). One unit of enzyme hydrolyzes 1.0 micromole ($\mu$mole) of o-nitrophenyl-$\beta$-D-galactoside per minute when assayed at 25° C. in 50 millimolar (mM) Bicine buffer [N,N-bis-(2-hydroxyethyl)glycine from Calbiochem], pH 8.5, containing 3 mM o-nitrophenyl-$\beta$-D-galactoside.

3. Buffer—Bicine buffer was used at 50 mmolar, pH 8.5, at 25° C.

4. IgG standards—Pooled sera diluted 100-fold with the buffer.

5. Fluorogenic IgG Reagent—$\beta$-Galactosyl-umbelliferone-labeled IgG from Example 1.

B. Assay Procedure and Results

To a plastic disposable cuvette was added sequentially 3.1 ml of the buffer containing 0.28 nmole (89 nM) of the Fluorogenic IgG Reagent, 0.1 ml of a selected standard, and 0.1 ml of the antiserum diluted 10-fold with the buffer (sufficient to decrease the enzyme reaction to about 10% of that observed in the absence of antiserum). The cuvette was gently inverted for mixing and 0.1 ml of the enzyme solution containing 0.005 unit of $\beta$-galactosidase was added and mixed by inversion. The solution was incubated at room temperature for 30 minutes and the fluorescence intensity measured with an Aminco-Bowman spectrofluorometer. Excitation and emission wavelengths were set at 400 and 450 nm, respectively, and all measurements were conducted at 25° C. A series of standards were assayed in this manner.

The results obtained were as follows:

| Concentration of IgG (mg/ml) | Fluorescence Units |
|---|---|
| 0 | 31 |
| 2 | 35 |
| 4 | 43 |
| 8 | 61 |
| 13 | 81 |
| 20 | 102 |

EXAMPLE 4

Assay for IgA

A. Assay Reagents

1. Antiserum—Alpha-chain specific antiserum from Cappel Laboratories, Cochranville, Pa.

2. Enzyme—Same as in Part A-2 of Example 3.

3. Buffer—Bicine buffer was used at 20 mM, pH 7.3, containing 4% weight per volume (w/v) of polyethylene glycol (average molecular weight—6000).

4. IgA standards—Diluted in 50 mM Bicine buffer, pH 8.2.

5. Fluorogenic IgA Reagent—$\beta$-Galactosyl-umbelliferone-labeled IgA from Example 2.

B. Assay Procedure and Results

To a cuvette containing 3.0 ml of the buffer was added a selected standard and 5 microliter ($\mu$l) of antiserum, and the solution mixed. To the mixture was added 45 $\mu$l of the Fluorogenic IgA Reagent (having an absorbance of 0.05 at 340 nm) followed by mixing and addition of 100 $\mu$l of $\beta$-galactosidase solution (1 unit/ml). The solution was incubated at room temperature for 30 minutes and the fluorescence intensity measured as in Example 3. A series of standards was assayed in this manner. The results obtained were as follows:

| Amount of IgA added ($\mu$g) | Fluorescence Units |
|---|---|
| 0 | 35 |
| 2 | 47 |
| 5 | 57 |
| 10 | 70 |
| 20 | 74 |
| 50 | 81 |

EXAMPLE 5

Assay for IgM

A. Assay Reagents

1. Antiserum—Obtained from DAKO-immunoglobulins, Copenhagen, Denmark.

2. Enzyme—Same as in Part A-2 of Example 3.

3. Buffer—Bicine buffer was used at 50 mM, pH 8.2.

4. IgM standards—Diluted in 50 mM Bicine buffer, pH 8.2.

5. Fluorogenic IgM Reagent—$\beta$-Galactosyl-umbelliferone-labeled IgM from Example 2.

B. Assay Procedure and Results

To a cuvette containing 3.0 ml of the buffer was added 100 $\mu$l of a selected standard and 5 $\mu$l of antiserum, and the solution mixed. To the mixture was added 100 $\mu$l of the Fluorogenic IgM Reagent (having an absorption of 0.02 at 340 nm) followed by mixing and addition of 100 $\mu$l of $\beta$-galactosidase solution (0.05 unit/ml). The solution was incubated for 30 minutes and the fluorescence intensity measured as in Example 3. A series of standards was assayed in this manner.

The results obtained were as follows:

| Amount of IgM added (μg) | Fluorescence Units |
| --- | --- |
| 0 | 15 |
| 2 | 23 |
| 5 | 34 |
| 7 | 43 |
| 10 | 47 |
| 20 | 50 |
| 30 | 60 |
| 50 | 61 |

Thus, it was demonstrated that the present invention provides labeled proteins useful as reagents in specific binding assays.

What is claimed is:

1. A β-galactosyl-umbelliferone-labeled conjugate of the formula:

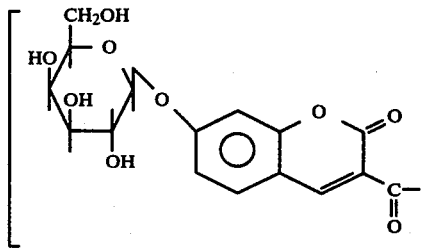

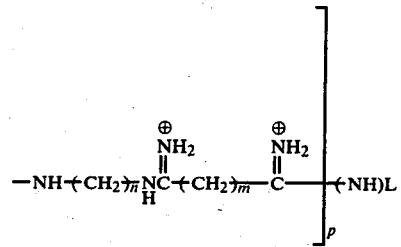

wherein $-(NH)L$ is a protein or polypeptide bound through an amino group thereof whereby said protein or polypeptide in the conjugate is capable of being bound by an antibody, n is an integer from 2 through 10, m is an integer from 1 through 10, and p is on the average from 1 to the number of available amino groups in L.

2. The conjugate of claim 1 wherein $-(NH)L$ is a protein or polypeptide of molecular weight between 130 and 10,000,000.

3. The conjugate of claim 1 wherein $-(NH)L$ is a protein or polypeptide of molecular weight between 1,000 and 1,000,000.

4. The conjugate of claim 1 wherein $-(NH)L$ is an immunoglobulin.

5. The conjugate of claim 4 wherein said immunoglobulin is IgG.

6. The conjugate of claim 4 wherein said immunoglobulin is IgM.

7. The conjugate of claim 4 wherein said immunoglobulin is IgA.

8. The conjugate of any of claims 1–7 wherein p is on the average from 1 to 100.

9. The conjugate of any of claims 1–7 wherein p is on the average from 1 to 20.

10. The conjugate of claim 9 wherein n=6 and m=4.

11. The conjugate of any of claims 1–7 wherein n=6 and m=4.

* * * * *